(12) United States Patent  (10) Patent No.: US 8,641,277 B2
Simmons et al.  (45) Date of Patent: Feb. 4, 2014

(54) SLIDING COUNTERBALANCED C-ARM POSITIONING DEVICES AND METHODS FOR USING SUCH DEVICES

(71) Applicant: General Electric Corporation, Schenectady, NY (US)

(72) Inventors: John Matthew Simmons, Bountiful, UT (US); David Barker, Salt Lake City, UT (US); Jan Bruening, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/856,221

(22) Filed: Apr. 3, 2013

(65) Prior Publication Data

US 2013/0223598 A1 Aug. 29, 2013

Related U.S. Application Data

(63) Continuation of application No. 13/036,946, filed on Feb. 28, 2011, now Pat. No. 8,430,564.

(51) Int. Cl.
 *H05G 1/02* (2006.01)
(52) U.S. Cl.
 USPC .......................................................... 378/198
(58) Field of Classification Search
 USPC .......................................... 378/198, 197, 196
 See application file for complete search history.

(56) References Cited

U.S. PATENT DOCUMENTS

| | | | |
|---|---|---|---|
| 4,868,845 A | 9/1989 | Koropp | |
| 4,872,192 A | 10/1989 | Hahn et al. | |
| 5,031,202 A | 7/1991 | Ohlson | |
| 5,050,204 A | 9/1991 | Siczek et al. | |
| 5,475,730 A | 12/1995 | Galando | |
| 5,627,873 A | 5/1997 | Hanover et al. | |
| 6,007,243 A | 12/1999 | Ergun et al. | |
| 6,234,672 B1 | 5/2001 | Tomasetti et al. | |
| 6,302,581 B1 * | 10/2001 | Sliski et al. | 378/198 |
| 8,430,564 B2 | 4/2013 | Simmons et al. | |

* cited by examiner

*Primary Examiner* — Irakli Kiknadze
(74) *Attorney, Agent, or Firm* — Kenneth E. Horton; Kirton McConkie (57) ABSTRACT

Systems and methods for making and using sliding counterbalanced C-arm positioning devices are described. In such systems and methods, each C-arm positioning device includes a C-arm X-ray device, a linear bearing rail, a linear bearing block, and a counterbalance mechanism. Generally, the C-arm is connected to the linear bearing block, which, in turn, is slidably coupled to the bearing rail to allow the bearing block and C-arm to slide up and down on the rail. The counterbalance mechanism can apply a force to the bearing block to counterbalance the weight of the C-arm and the bearing block. Thus, the described C-arm positioning device can allow a user to easily raise or lower the C-arm with relatively little effort. While some implementations of the C-arm positioning device are connected to mobile support structure, other implementations of the C-arm positioning device are mounted to a fixed support structure. Other implementations are also described.

20 Claims, 8 Drawing Sheets

SLIDING COUNTERBALANCED C-ARM POSITIONING DEVICES AND METHODS FOR USING SUCH DEVICES

This application is a continuation application of U.S. application Ser. No. 13/036,946, filed on Feb. 28, 2011, the entire disclosure of which is incorporated herein by reference.

FIELD

This application relates generally to X-ray equipment. More specifically, this application relates to sliding counterbalanced C-arm positioning devices that allow their users to easily raise and lower a C-arm of an X-ray machine.

BACKGROUND

X-ray machines are known devices that allow individuals, such as healthcare practitioners, to capture images, in a relatively non-intrusive manner, of bones, bone density, implanted devices, catheters, pins, and a wide variety of other objects and materials that are within a patient's body. In this regard, the term X-ray may refer to any suitable type of X-ray imaging, including film X-ray shadow grams and X-ray fluoroscopic imaging, which may refer to images that are produced by the conversion of an incident X-ray pattern to a "live" enhanced or intensified optical image that can be displayed on a video monitor, nearly contemporaneously with the irradiation of the portion of the patient's body that is being imaged.

Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned.

SUMMARY

This application relates to X-ray positioning devices. In particular, this application discusses systems and methods for making and using sliding, counterbalanced C-arm positioning devices. In such systems and methods, each C-arm positioning device comprises a C-arm X-ray device, a linear bearing rail, a linear bearing block, and a counterbalance mechanism. Generally, the C-arm can be connected (directly or indirectly) to the linear bearing block, which, in turn, can be slidably coupled to the linear bearing rail. In this manner, the linear bearing block can slide up and down the rail to raise and lower the C-arm. The counterbalance mechanism can be configured to apply a force to the linear bearing block to substantially counterbalance the weight of the C-arm and the bearing block. Thus, the described C-arm positioning device can allow a user to easily raise and lower the C-arm with relatively little effort. Additionally, while some implementations of the C-arm positioning device are connected to a mobile support structure, in other implementations, the C-arm positioning device is mounted to a fixed support structure.

BRIEF DESCRIPTION OF THE DRAWINGS

The following description can be better understood in light of the Figures, in which.

The Figures illustrate specific aspects of the described sliding C-arm positioning devices and methods for making and using such devices. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described C-arm positioning devices and associated methods of making and using the devices can be implemented and used without employing these specific details. Indeed, the sliding counterbalanced C-arm positioning devices and associated methods can be placed into practice by modifying the described devices and methods and can be used in conjunction with any other apparatus and techniques conventionally used in the industry. For example, while the description below focuses on methods for making and using the C-arm positioning device for mini C-arms, the C-arm positioning device can be used with standard C-arm devices.

The present application describes sliding counterbalanced imaging arm positioning devices that allow a user to raise and lower the X-ray assembly in the imaging arm with relatively little physical effort. The positioning device can be used with any type of imaging arm, including an O-arm or a C-arm. In some embodiments, the positioning device can be used with C-arm devices.

Figures 1, 2:
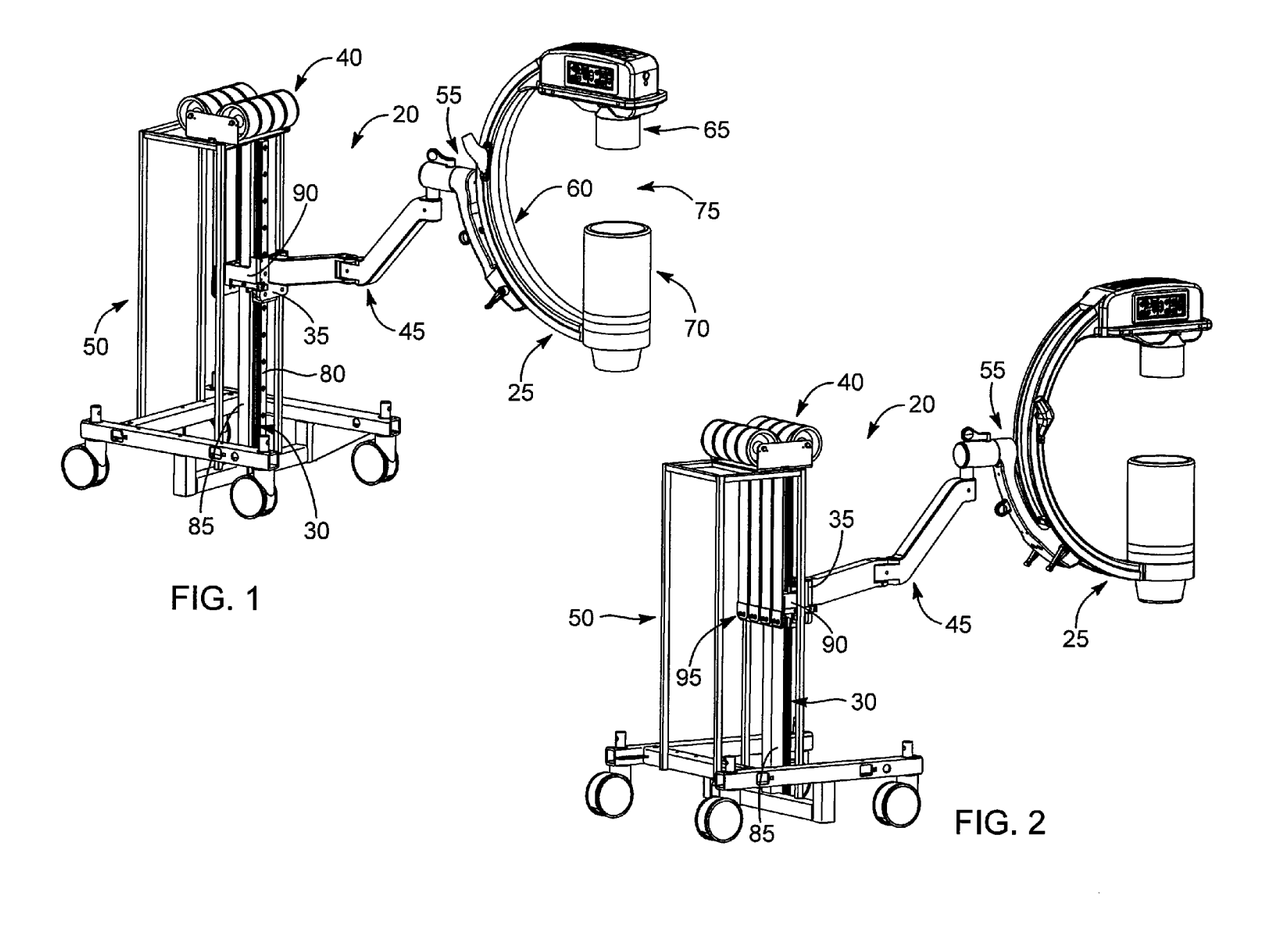
FIG. 1 shows a front perspective view of some embodiments of a sliding C-arm positioning device having a counterbalance mechanism that is at least partially disposed above a linear bearing block.
FIG. 2 shows a side perspective view of the C-arm positioning device of FIG. 1.

While the described sliding counterbalanced C-arm positioning devices can comprise any suitable component that allows the devices to provide this function, FIG. 1 shows some embodiments in which the sliding counterbalanced C-arm positioning device (or C-arm positioning device) 20 comprises a C-arm X-ray assembly (or C-arm) 25, a linear bearing rail assembly 30, a linear bearing block 35, and a counterbalance mechanism 40. FIG. 1 also shows that, in some embodiments, the C-arm positioning device 20 optionally comprises a C-arm support arm 45, a bearing rail support structure 50, and/or a C-arm rotational system 55. To provide a better understanding of the C-arm positioning device, each of the aforementioned components is described below in more detail.

The C-arm 25 can comprise any suitable C-arm that allows the C-arm positioning device 20 to be used to take X-ray images of a portion of a patient's body (not shown). For example, the C-arm can comprise a mini C-arm, a standard C-arm, a fixed x-ray detector and source structure, a variable x-ray detector and source structure and/or any other suitable type of C-arm X-ray assembly. By way of illustration, FIG. 1 shows some embodiments in which the C-arm 25 comprises a mini C-arm 60.

The C-arm 25 can also comprise any suitable component that allows it to function as intended. For example, FIG. 1 shows some embodiments in which the C-arm 25 comprises an X-ray source 65 and an X-ray image detector 70 that are respectively disposed at nearly opposite ends of the C-arm so as to face each other. The X-ray image detector can be any known detector, including a digital flat panel detector or an image intensifier. FIG. 1 also shows that the X-ray source 65 and image detector 70 are spaced apart to define a gap 75 that is large enough to allow a portion of a patient's body (e.g., a limb, an extremity, etc.) to be inserted into the path of the X-ray beam (not shown) for X-ray imaging.

The linear bearing rail assembly 30 can serve any suitable purpose, including providing a guide, support, and/or rail on which the linear bearing block 35 (described below) and C-arm 25 can slide in two directions (e.g., vertically up and down). In this regard, the linear bearing rail assembly can comprise any suitable component that allows the assembly to function as intended. By way of illustration, FIG. 1 shows some embodiments in which the linear bearing rail assembly 30 comprises a linear bearing rail 80 and optionally comprises a linear bearing rail spine 85.

The linear bearing rail 80 can comprise any known or novel linear bearing rail that can be coupled to the linear bearing block 35 in a manner that allows the bearing block and C-arm to be raised and lowered in the manner described herein. Indeed, some examples of suitable linear bearing rails include one or more conventional or novel T-rails, U-rails, T+U rails, V-rails, monorails, telescopic drawer slides, linear slides, roller embossed rails, round shaft rails (i.e., single rail, double rail, etc.), square shaft rails (i.e., single rail, double rail, etc.), threaded shaft, helical shaft, or any combination thereof. By way of illustration, FIG. 1 shows some embodiments in which the linear bearing rail 80 comprises a linear bearing or linear guide.

The linear bearing rail 80 can have any suitable characteristic that allows it to fulfill its intended purpose. In one example, the linear bearing rail can comprise one or more grooves that are sized and shaped to receive rollers (e.g., wheels, bearings, etc.) from the linear bearing block 35. In another example, the linear bearing rail comprises one or more raised rails that fit within one or more corresponding roller mechanisms (e.g., one or more wheels, bearing raceways, etc.) of the linear bearing block. In still another example, the linear bearing rail 80 can be any suitable length. Indeed, in some embodiments, the linear bearing rail can be a length selected from about 10 inches, about 24 inches, about 34 inches, about 48 inches, about 56 inches, about 120 inches, and any suitable combination or sub-range of the these lengths. For instance, some embodiments of the linear bearing rail can be about 24, about 36, or about 48 inches.

Where the linear bearing rail assembly 30 comprises a spine 85, the spine can serve any suitable purpose, including acting to physically support the linear bearing rail 80. Moreover, where the linear bearing rail assembly includes the spine, the spine can comprise any suitable component that is capable of physically supporting the linear bearing rail. By way of example, the spine can comprise a solid shaft/bar, a hollow pipe/tube, a rail, a guide, a dovetail, a combination of these elements, and/or any other suitable support.

The linear bearing block 35 can serve any suitable purpose, including slidably attaching the C-arm 25 to the linear bearing rail 80 to allow the C-arm to be moved in two directions (e.g., vertically up and down). Accordingly, the linear bearing block can comprise any suitable component that allows it to slidably couple with the linear bearing rail and to connect to and support the weight of the C-arm. Indeed, in some embodiments, the linear bearing block comprises one or more rollers (e.g., bearings, wheels, ball guides with balls, linear ball bearings, etc.). Moreover, in some embodiments, the linear bearing block is configured to slidably couple with the linear bearing rail by having one end of the rail inserted into the block.

Because the linear bearing rail 80 can be any suitable length (as discussed above), the linear bearing block 35 can have any suitable maximum range of movement, or stroke. Indeed, in some implementations, the linear bearing block has a stroke that is substantially equal to the length of the linear bearing rail less the height of the linear bearing block. Accordingly, in some embodiments, the linear bearing block has a stroke with a length selected from about 10 inches, about 12 inches, about 24 inches, about 36 inches, about 48 inches, about 60 inches, about 80 inches, about 100 inches, and about 120 inches. In this regard, the linear bearing block can have any suitable stroke that falls within any suitable combination or sub-range of the aforementioned stroke lengths. For instance, some embodiments of the C-arm positioning device have a linear bearing block having a stroke that is greater than about 24 and less than about 48 inches (e.g., about 36±5 inches). In still other embodiments, the linear bearing block has a stroke that is longer than about 32 inches (e.g., longer than about 34 inches) and less than about 44 inches.

Figure 3A:
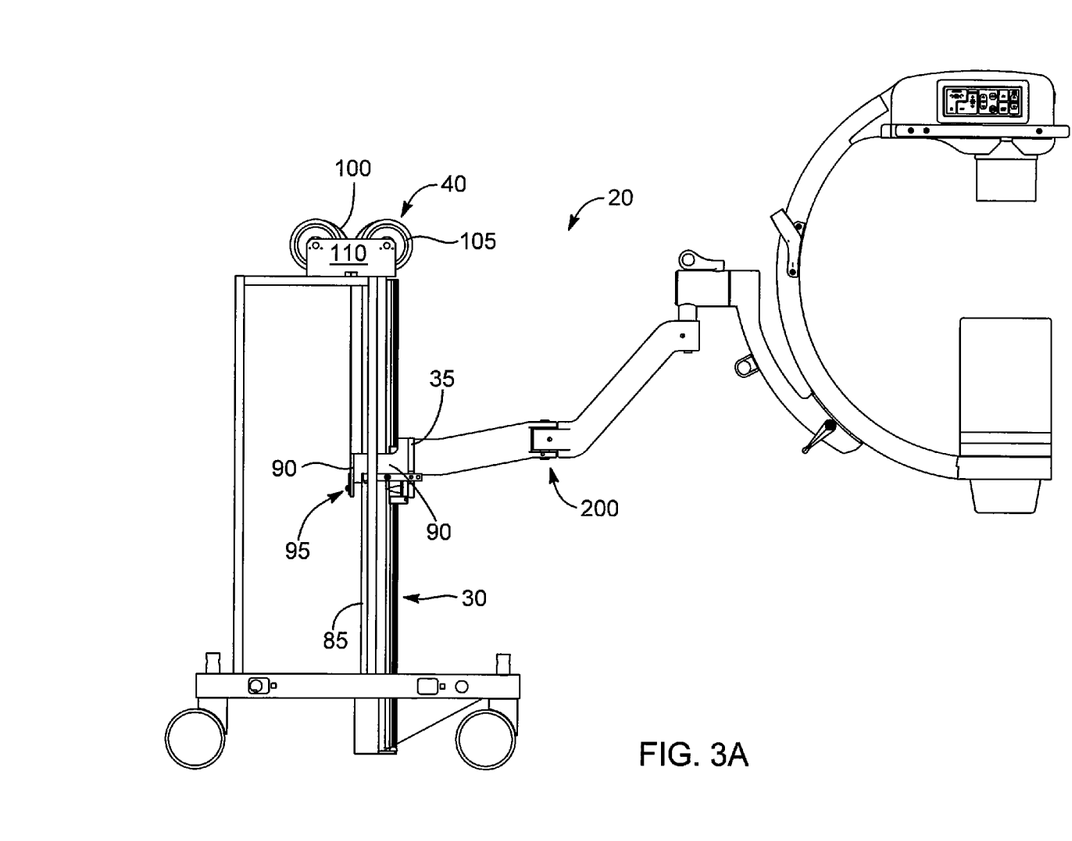
FIG. 3A shows a side plan view of the C-arm positioning device of FIG. 1.
Figure 3B:
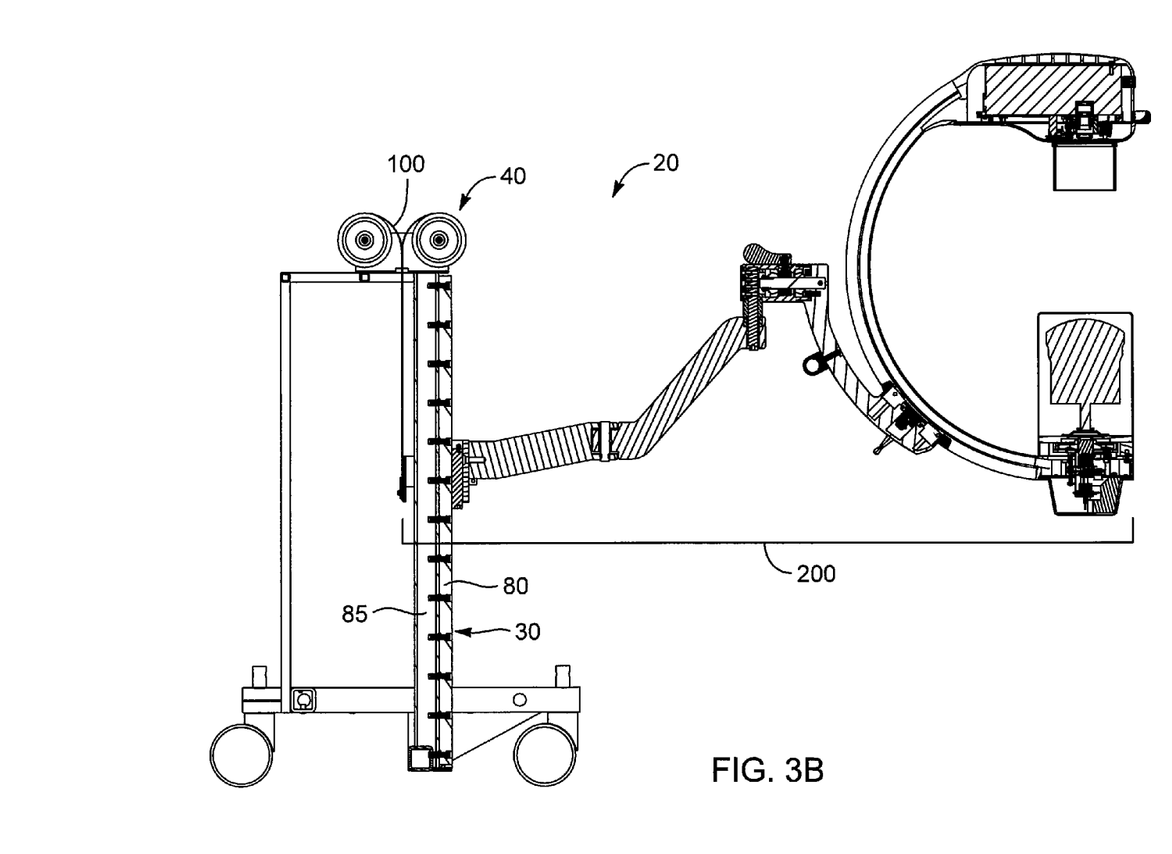
FIG. 3B shows a cross-sectional side view of the C-arm positioning device of FIG. 1.
Figure 4:
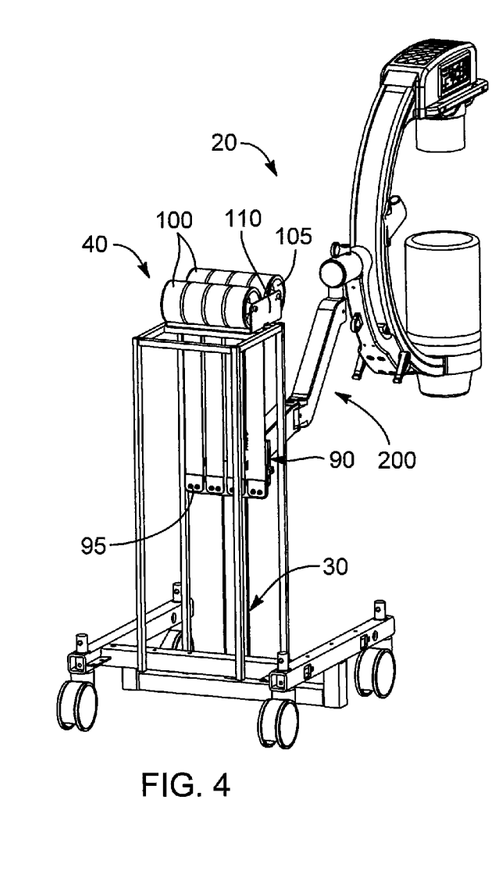
FIG. 4 shows a back perspective view of the C-arm positioning device of FIG. 1.

The linear bearing block 35 can also comprise any other suitable component or characteristic that allows it to function as intended. For instance, FIGS. 1 and 2 shows some embodiments in which the linear bearing block 35 comprises a carriage 90. In such embodiments, the carriage can perform any suitable function, including serving as a connection point for the counterbalance mechanism 40 and/or a brake system (e.g., to stop the vertical movement of the linear bearing block). To this end, the carriage can have any suitable characteristic that allows it to perform its intended functions. For example, FIGS. 3A through 4 show that the carriage 90 can wrap around at least a portion of the linear bearing rail assembly 30 and serve as a connection point 95 for the counterbalance mechanism 40 on the linear bearing block.

The counterbalance mechanism 40 can serve any suitable purpose. Indeed, in some embodiments, the counterbalance mechanism applies a force to the linear bearing block 35 (directly or indirectly) to counterbalance at least a portion of the weight of the linear bearing block, the C-arm 25, and/or any other component or components of the C-arm positioning device 20 that rest their weight on the linear bearing block (e.g., the C-arm support arm 45, power cables, etc.), collectively referred to herein as the linear bearing block assembly 200.

Where the counterbalance mechanism 40 counterbalances the weight of the linear bearing block assembly 200, a user can raise or lower the C-arm 25 with relatively little effort. Furthermore, where the counterbalance mechanism counterbalances the weight of the linear bearing block assembly, the counterbalance mechanism can help maintain the position of the linear bearing block 35 with respect to the linear bearing rail 80. In this manner, the counterbalance mechanism can help prevent the linear bearing block from creeping down (due to the force of gravity on the linear bearing block assembly being greater than the upward force of the counterbalance mechanism on the linear bearing block) and from creeping up on the rail (due to the upward force of the counterbalance mechanism being greater than the force of gravity on the linear bearing block assembly).

The counterbalance mechanism 40 can comprise any suitable component that allows it to substantially counterbalance the weight of the linear bearing block assembly 200. Some examples of suitable counterbalance mechanisms comprise one or more constant force springs, spring motors, gas springs, tension springs, torsion springs, compression springs, cams, hydraulic circuits, weights, pulleys and a cable, and/or any other suitable component that allows the counterbalance mechanism to fulfill its intended purpose.

In one example of a suitable counterbalance mechanism 40, FIGS. 3A through 4 show some embodiments in which the counterbalance mechanism 40 comprises one or more constant force springs 100. A constant force spring may comprise virtually any suitable spring that exerts a substantially constant force over its range of motion. That said, in some embodiments, each of the constant force springs is generally constructed as a rolled ribbon of spring steel.

Where the counterbalance mechanism 40 comprises one or more constant force springs 100, the mechanism can comprise any suitable number of constant force springs that allows it to substantially counterbalance the weight of the linear bearing block assembly 200. For instance, the counterbalance mechanism can comprise 1, 2, 3, 4, 5, 6, 7, 8, . . . 20, or more constant force springs. Indeed, FIG. 4 shows some embodiments in which the counterbalance mechanism 40 comprises 8 constant force springs 100. In any case, in order to counterbalance the weight of the linear bearing block assembly, the total upward force that the springs exert on the linear bearing block 35 is substantially equal to the weight of the linear bearing block assembly.

Where the counterbalance mechanism 40 comprises one or more constant force springs 100, the mechanism can also comprise any other suitable component that allows the C-arm positioning device 20 to function as intended. By way of illustration, FIG. 4 shows some embodiments in which each of the constant force springs 100 of the counterbalance mechanism 40 is configured to coil on a rotating spool 105 that is mounted to the C-arm positioning device 20 (e.g., via bracket 110). Furthermore, while the constant force springs can be assembled in the counterbalance mechanism in any suitable manner, FIG. 4 further shows some embodiments in which pairs of corresponding constant force springs 100 coil in opposite directions so that springs from a corresponding pair of coils can easily be connected to the same connection point 95.

Figure 5:
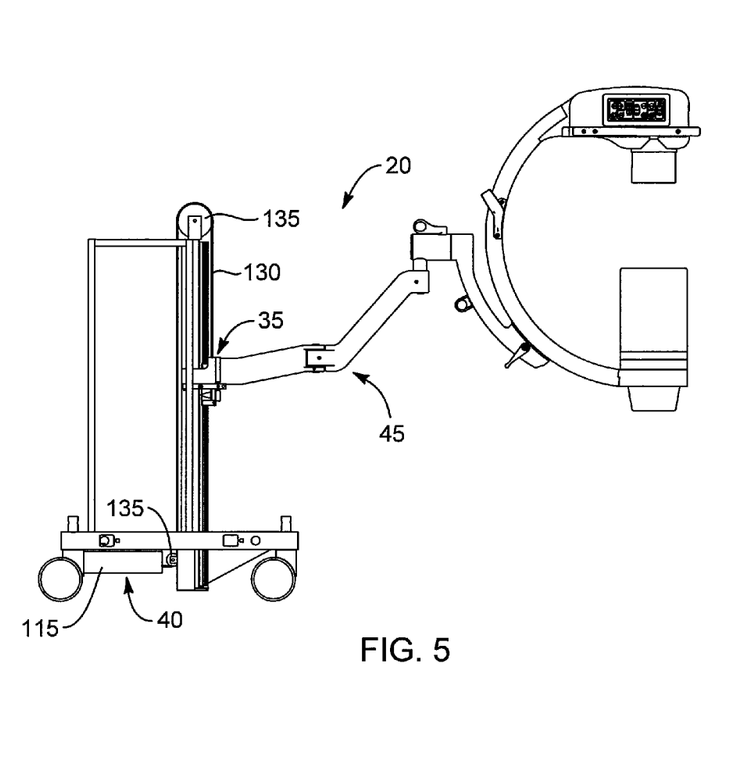
FIG. 5 shows a side plan view of some embodiments of a sliding C-arm positioning device having the counterbalance mechanism that is at least partially disposed below the linear bearing block.
Figure 6:
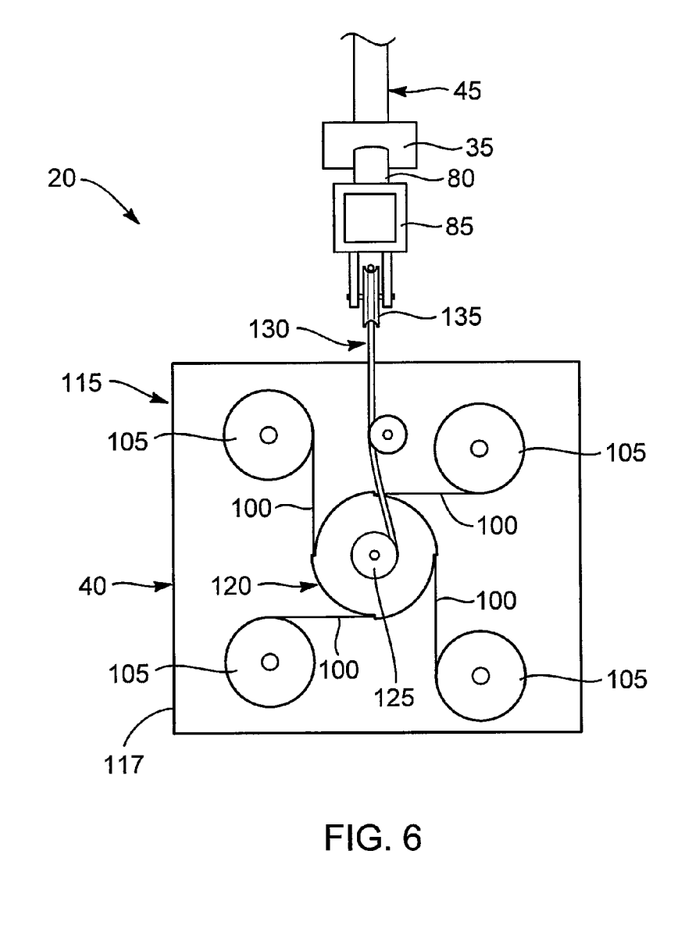
FIG. 6 shows a bottom plan view of some embodiments of a portion of the sliding C-arm positioning device that have a spring motor.

In another example of a suitable counterbalance mechanism 40, FIGS. 5 and 6 show some embodiments in which the counterbalance mechanism 40 comprises a spring motor 115. In such embodiments, the spring motor can have any suitable characteristic consistent with its function described herein. By way of illustration, FIG. 6 (which shows a bottom view of only some components of the C-arm positioning device 20 of FIG. 5) shows some embodiments in which the spring motor 115 comprises a housing 117 containing 4 constant force springs 100 that are each coiled around a rotating spool 105 and connected to a constant force spring drum 120, which, in turn, is fixed with respect to a flexible connector drum 125. In these embodiments, as the flexible connector (e.g., cable 130) is unwound from the flexible connector drum, the constant force springs are uncoiled from their respective constant force spools and are wound, at least partially, on the constant force spring drum—thus allowing the C-arm 25 to be lowered.

While FIG. 6 shows some embodiments of the spring motor 115 that comprise 4 constant force springs 100, the spring motor may be modified in any suitable manner that allows it to perform its intended function. For example, the spring motor can comprise 1, 2, 3, 4, 5, 6, 7, 8, or more constant force springs, which are each attached to the constant force spring drum 120.

The counterbalance mechanism 40 can be disposed in any suitable location that allows it to function as intended. Indeed, while in some embodiments, the counterbalance mechanism is disposed at least partially above the linear bearing block 35, as shown in FIG. 4. In other embodiments, the counterbalance mechanism 40 can be located below or to the side of the linear bearing block, as shown in FIG. 5. In one example, FIG. 4 shows the counterbalance mechanism 40 is mounted above the linear bearing block 35 to allow the constant force springs 100 to coil above the linear bearing block. In another example, FIG. 4 shows the springs (not shown) of the mechanism 40 are able to coil at least partially, below the linear bearing block 35. In another example, which is not illustrated, the counterbalance mechanism is mounted on the linear bearing block (e.g., so as to coil at the block) and/or the C-arm support arm assembly 45.

Despite the location of the counterbalance mechanism 40, the mechanism can be connected to the linear bearing block 35 in any suitable manner that allows it to apply an upward force to the linear bearing block 35. In one example, springs 100 extending from the counterbalance mechanism are attached to the linear bearing block (directly or indirectly). By way of illustration, FIG. 4 shows some embodiments in which constant force springs 100 from the counterbalance mechanism 40 are attached to the linear bearing block 35 (e.g., via the carriage 90) at connection point 95.

In another example, the counterbalance mechanism 40 uses one or more flexible connectors (e.g., one or more cables, roller chains, belts, and/or any other suitable components) to apply a counterbalancing force to the linear bearing block 35. In this example, the C-arm positioning device 20 can optionally comprise one or more rotating wheels (e.g., pulleys, gears, spools, and/or any other suitable rotating components) to change the direction of the flexible connector so as to allow the counterbalance mechanism to apply an upward force to the linear bearing block, despite the mechanism's position. By way of illustration, FIG. 5 shows some embodiments in which a cable 130 extends between the spring motor 115 and the linear bearing block 35, using multiple pulleys 135 to redirect the cable.

In some embodiments, the C-arm 25 (or the C-arm rotational system 55) are connected directly to the linear bearing block 35. In other embodiments, the C-arm support arm 45 connects the C-arm to the linear bearing block. In these latter embodiments, the C-arm support arm can have any suitable component or characteristic. By way of example, the C-arm support arm can have any suitable number of elongated sections and can optionally have any suitable number or type of pivot joints. For instance, FIGS. 7 and 8 show some embodiments in which the C-arm support arm 45 comprises a first elongated section 140 and a second elongated section 145.

Where the C-arm support arm 45 comprises a first elongated section 140, that section can comprise any suitable component or characteristic. In one example, while the first elongated section can be pivotally attached to the linear bearing block 35, FIGS. 7 and 8 show some embodiments in which the first elongated section 140 is fixed in position with respect to the linear bearing block 35. In another example, FIGS. 7 and 8 show that the first elongated section 140 can comprise a pivot joint 146 that pivotally attaches to the second elongated section 145 to allow the second elongated section to pivot horizontally through an arc of motion.

The second elongated section 145 can comprise any suitable component or characteristic. By way of illustration, FIGS. 7 and 8 show some embodiments in which the second elongated section 145 is pivotally connected to the C-arm rotational system 55 (e.g., via pivot joint 148) to allow the C-arm rotational system and C-arm 25 to pivot horizontally through an arc of motion.

Figure 7:
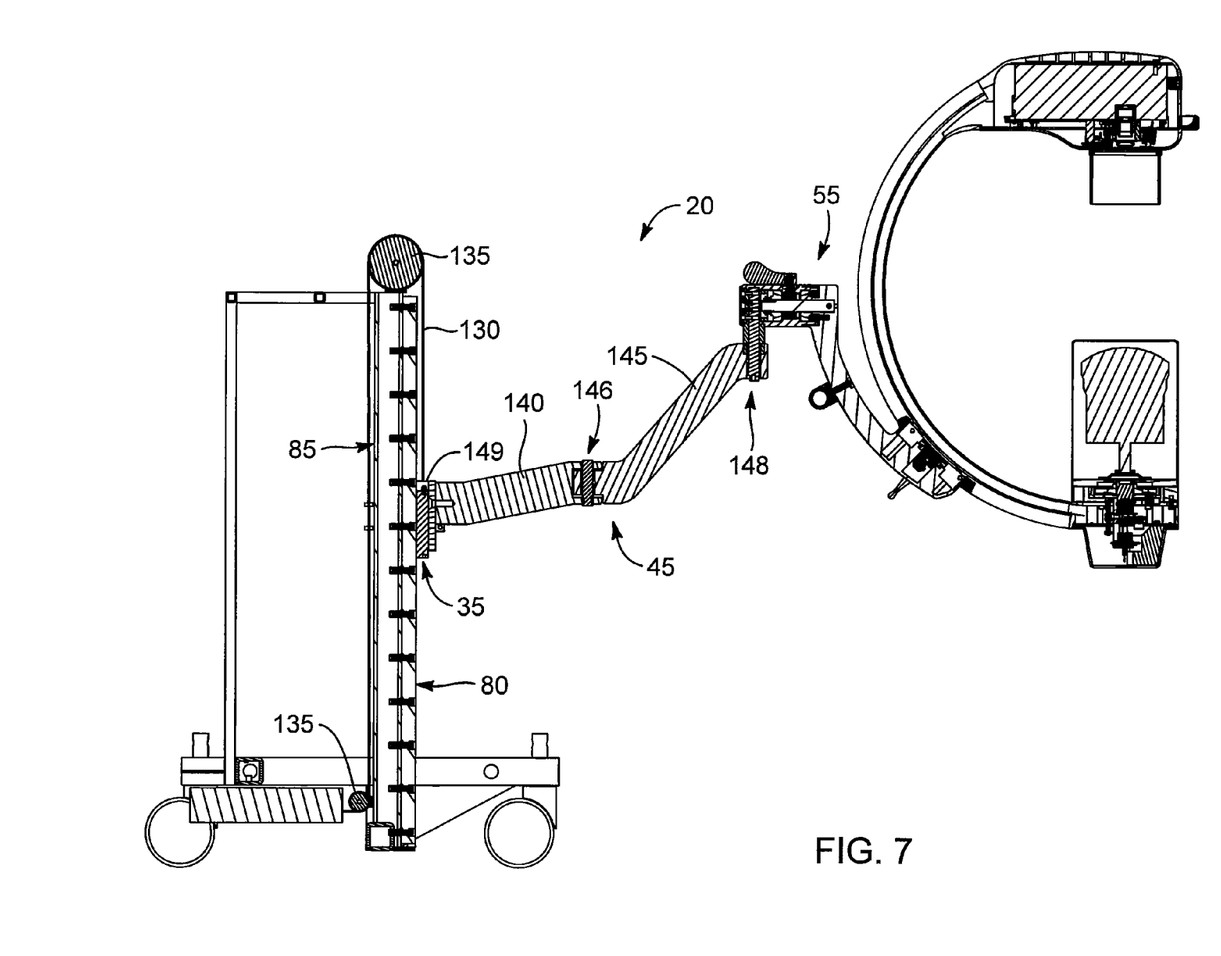
FIG. 7 shows a cross-sectional side view of the C-arm positioning device of FIG. 5.
Figure 8:
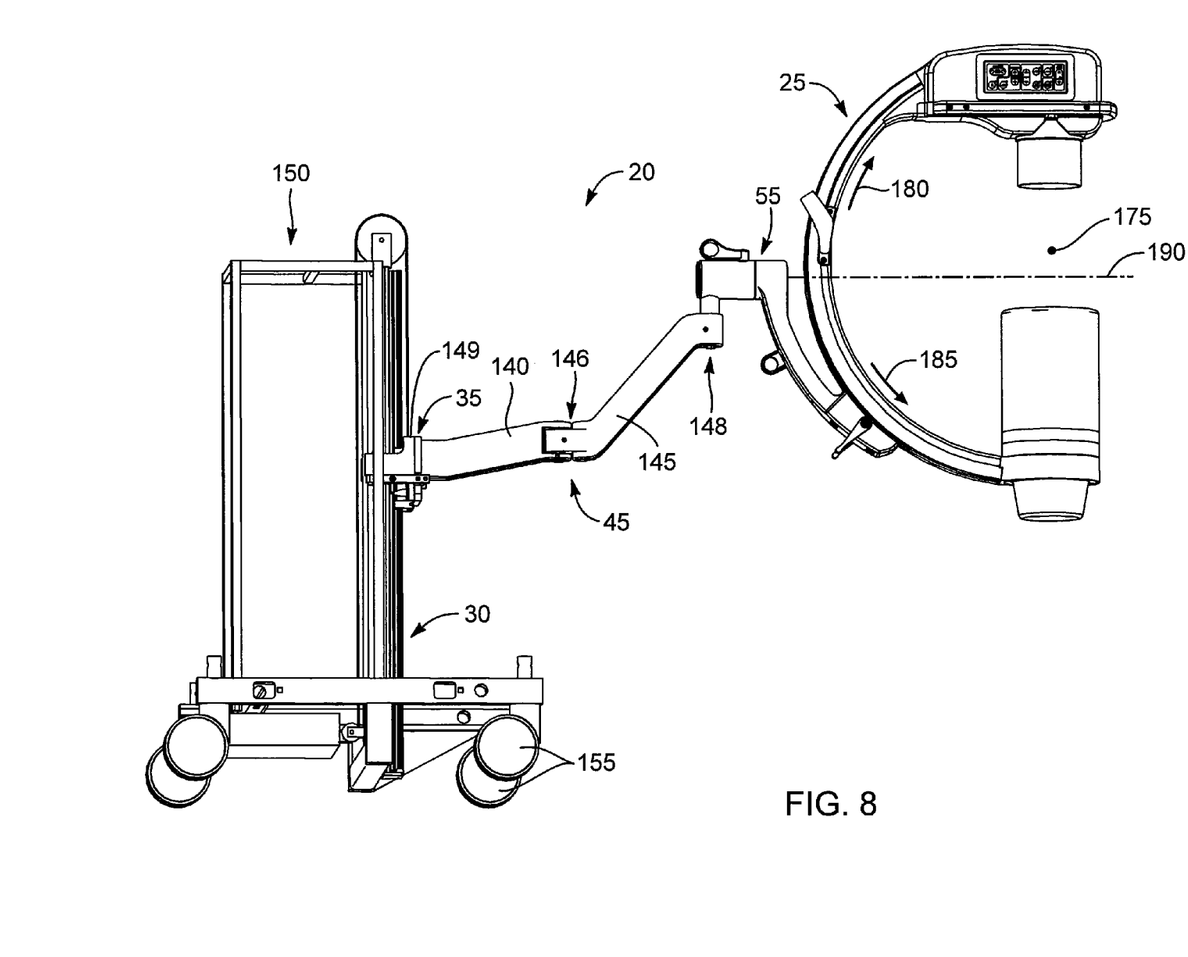
FIG. 8 shows a side perspective view of the C-arm positioning device of FIG. 5.

In another example of a suitable characteristic of the second elongated section 145, FIGS. 7 and 8 show that the second elongated section 145 is optionally permanently angled so as to rise above an upper edge 149 of the linear bearing block 35. In this manner, the second elongated member can allow the stroke of the linear bearing block to extend lower on the linear bearing rail 80 without allowing the C-arm to be damaged by allowing it to strike the floor (not shown).

In order to keep the linear bearing rail 80 in a desired orientation (e.g., substantially vertical), the linear bearing rail (and/or spine 85) can be connected to any suitable bearing rail support structure 50. Indeed, in some implementations, the linear bearing rail is connected to a fixed support structure, such as a wall, a column, a floor, a shelf, a cabinet, a stationary frame, and/or any other suitable support structure that is not intended to be easily moved and repositioned around a patient.

In other implementations, however, the linear bearing rail 80 (and/or spine 85) is connected to a movable support structure. In such implementations, the movable support structure can comprise any suitable characteristic that allows it to move across a floor while supporting the linear bearing rail and any objects supported therefrom (e.g., the linear bearing block assembly 200). Thus, the movable support structure can comprise one or more wheels, shelves, handles, weights to prevent the weight of the C-arm from tipping the movable support structure, and/or any other suitable components. By way of illustration, FIG. 8 shows some embodiments in which the movable support structure 150 comprises a wheeled framework that supports linear bearing rail assembly 30. FIG. 8 also shows some embodiments in which two of the wheels 155 extend past the linear bearing rail assembly 30 to prevent the weight of the C-arm 25 from causing the movable support structure 150 to tip. In some embodiments, the mobile structure should be configured so that the center of gravity is located within the footprint of the wheels.

As previously mentioned, the C-arm positioning device 20 can also comprise a C-arm rotational system 55. In this regard, the C-arm rotational system can comprise any known or novel C-arm rotational system that allows the C-arm to be repositioned on the linear bearing block 30 or at the end of the C-arm support arm 45. By way of illustration, FIG. 8 shows some embodiments in which the C-arm rotational system 55 is configured to allow the C-arm 25 to rotate orbitally about an axis of orbital rotation 175 in the direction of arrows 180 and 185, as well as to rotate around an axis of lateral rotation 190 to thereby rotate the C-arm 25 laterally.

Figure 9:
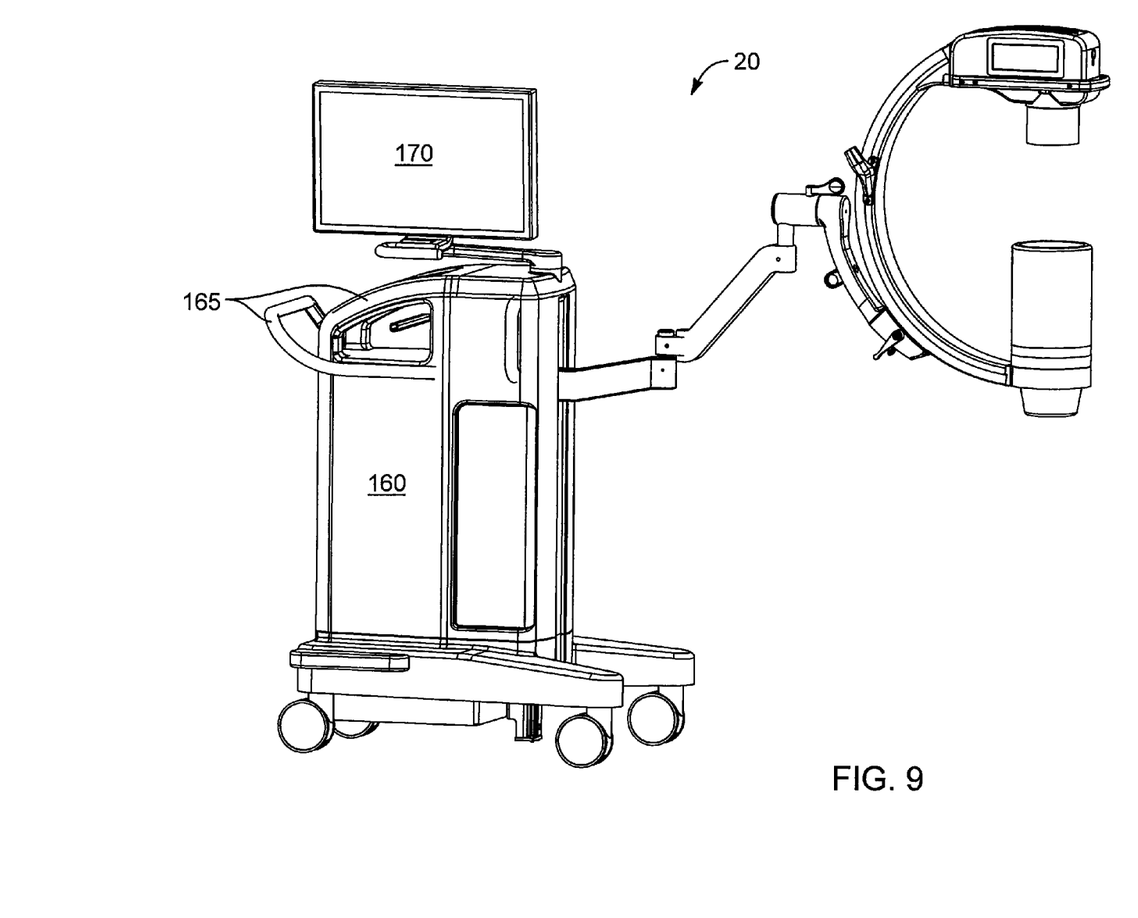
FIG. 9 shows a side perspective view of some embodiments of the C-arm positioning device comprising a cover and monitor.

In addition to the aforementioned components, the described C-arm positioning device 20 can comprise any other suitable component or characteristic known in the art. For example, the C-arm positioning device can comprise one or more support structure covers, monitors, handles, power supplies (e.g., internal and/or external), X-ray imaging systems, X-ray control devices, and linear bearing block brake systems. By way of illustration, FIG. 9 shows some embodiments in which the C-arm positioning device 20 comprises a support structure cover 160, handles 165, and a monitor 170.

The described C-arm positioning device 20 can be made in any manner that forms the structures described. By way of example, the C-arm positioning device can be formed through a process involving molding, extruding, casting, cutting, stamping, bending, drilling, bonding, welding, mechanically connecting, and/or any other suitable process.

The described C-arm positioning device 20 can also be used in any suitable manner. By way of example, an operator can raise and lower the C-arm by applying an upward and downward force, respectively, to a portion of the linear bearing assembly 200. Thus, the operator can use the C-arm positioning device 20 to quickly and efficiently move the C-arm to the desired portion of the patient needing to be analyzed.

The C-arm positioning device 20 may have several features. First, because the counterbalance mechanism 40 can substantially counterbalance the weight of the linear bearing block assembly 200, an operator can raise and lower the C-arm 25 with relatively little physical force. Accordingly, the process for using the described C-arm positioning device to raise and lower the C-arm which may not require a level of physical exertion that significantly detracts from other important tasks to be carried out by the operator.

Second, because the C-arm 25 in the described C-arm positioning device is connected to the linear bearing block 35, which in turn is slidably coupled to the linear bearing rail 80, the C-arm in the described device can move straight up and down and not through a vertical arc of motion as it is raised. Thus, unlike some conventional devices that are used to raise and lower a C-arm by causing the C-arm to move through an arc, the described C-arm positioning device can move the C-arm substantially straight up and down or in a substantially vertical direction. Accordingly, the described device may require less repositioning of the patient than may some conventional devices that are used to position a C-arm.

Third, where the counterbalance mechanism 40 comprises one or more constant force springs (i.e., within a spring motor), the counterbalance mechanism may not be subject to the shortcomings that are associated with certain gas springs. For example, unlike some gas springs that are affected by changes in temperature or elevation, the constant force springs are not. In another example, while some conventional gas springs need to be approximately 2 times longer than the stroke they provide, a counterbalance mechanism comprising constant force springs may only increase the height of the C-arm positioning device by a relatively small amount (if at all) over the stroke length of the linear bearing block. Accordingly, certain embodiments of the described device can easily be scaled to virtually any size (e.g., the stroke can be increased), without requiring space for a corresponding gas spring. In still another example, unlike some gas springs that tend to leak over time, the constant force springs may retain a significantly constant tension over their life. In yet another example, unlike some conventional devices that use one or more gas springs to hold the C-arm in position and that tend to allow the weight of the C-arm to compress the gas spring(s) and thereby cause the C-arm to slowly lower, constant force springs may not be subject to such compression. According, where the described counterbalance mechanism comprises one or more constant force springs, the mechanism may do a better job of retaining the C-arm at a desired height than a conventional device that uses one or more gas springs to retain the height of the C-arm.

A fourth feature is that since the counterbalance mechanism 40 comprises one or more constant force springs 100, the described C-arm positioning device 20 may be lighter and/or less expensive than some conventional devices that use one or more gas springs. Accordingly, the described C-arm positioning device may be easier to move and be less expensive than some other conventional devices that are used to reposition and support a C-arm.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A mobile X-ray imaging system, comprising:
    a mobile workstation comprising a substantially linear bearing rail;
    an imaging arm containing an x-ray source and detector, the imaging arm connected to a linear bearing block that is slidably coupled with the linear bearing rail; and
    a counterbalance capable of applying a force to the linear bearing block and counterbalancing a portion of the weight of the imaging arm and the linear bearing block.

2. The system of claim 1, wherein the counterbalance comprises a constant force spring.

3. The system of claim 2, wherein the constant force spring coils above the linear bearing block.

4. The system of claim 2, wherein the constant force spring does not coil above the linear bearing block.

5. The system of claim 1, wherein the counterbalance comprises a spring motor.

6. The system of claim 1, wherein the counterbalance is connected to the linear bearing block by a flexible connector that is guided to the linear bearing block by a rotatable wheel.

7. The system of claim 1, further comprising a support arm that pivotally connects the imaging arm to the linear bearing block.

8. The system of claim 1, wherein the imaging arm comprises a C-arm containing a support arm with an elongated section that is permanently angled to rise above an upper end of the linear bearing block.

9. The system of claim 1, wherein the mobile workstation comprises a support structure capable of preventing the weight of the imaging arm from tipping the mobile workstation.

10. An x-ray positioning device, comprising:
    a substantially linear bearing rail coupled to a mobile workstation;
    an imaging arm containing an x-ray source and detector, the imaging arm connected to a linear bearing block that is slidably coupled with the linear bearing rail; and
    a counterbalance capable of applying a force to the linear bearing block and counterbalancing a portion of the weight of the imaging arm and the linear bearing block.

11. The device of claim 10, wherein the counterbalance comprises a constant force spring.

12. The device of claim 11, wherein the constant force spring coils above the linear bearing block.

13. The device of claim 11, wherein the constant force spring does not coil above the linear bearing block.

14. The device of claim 10, wherein the counterbalance comprises a spring motor.

15. The device of claim 10, wherein the counterbalance is connected to the linear bearing block by a flexible connector that is guided to the linear bearing block by a rotatable wheel.

16. The device of claim 10, further comprising a support arm that pivotally connects the imaging arm to the linear bearing block.

17. The device of claim 10, wherein the imaging arm comprises a C-arm containing a support arm with an elongated section that is permanently angled to rise above an upper end of the linear bearing block.

18. The device of claim 10, wherein the bearing rail is coupled to a support structure of the mobile workstation, wherein the support structure is capable of preventing the weight of the imaging arm from tipping the workstation.

19. A method for using an X-ray positioning device, comprising:
    providing an X-ray positioning device comprising:
        a substantially linear bearing rail coupled to a mobile workstation;
        an imaging arm containing an x-ray source and detector, the imaging arm connected to a linear bearing block that is slidably coupled with the linear bearing rail;
        a counterbalance capable of applying a force to the linear bearing block and counterbalancing a portion of the weight of the imaging arm and the linear bearing block; and
    moving the linear bearing block substantially vertically.

20. The method of claim 19, wherein the linear bearing block comprises a vertical stroke that is greater than about 10 inches.

* * * * *